United States Patent [19]

Rüger et al.

[11] Patent Number: 5,114,962

[45] Date of Patent: May 19, 1992

[54] NEW AMINO ACID ESTERS, A PROCESS FOR THEIR PREPARATION, MEDICAMENTS CONTAINING THEM, AND THE USE THEREOF

[75] Inventors: Wolfgang Rüger, Kelkheim; Hansjörg Urbach, Kronberg/Taunus; Reinhard Becker, Wiesbaden; Franz Hock, Dieburg, all of Fed. Rep. of Germany

[73] Assignee: Hoechst Aktiengesellschaft, Frankfurt am Main, Fed. Rep. of Germany

[21] Appl. No.: 540,634

[22] Filed: Jun. 19, 1990

Related U.S. Application Data

[63] Continuation of Ser. No. 244,389, Sep. 14, 1988, abandoned.

[30] Foreign Application Priority Data

Sep. 16, 1987 [DE] Fed. Rep. of Germany ....... 3731085

[51] Int. Cl.$^5$ ............... A61K 31/475; C07D 209/12; C07D 209/14
[52] U.S. Cl. .................................. 514/412; 514/414; 514/415; 548/452; 548/465; 548/469; 548/494; 549/229
[58] Field of Search ........... 514/412, 414, 415; 548/452, 465, 469, 494; 549/229

[56] References Cited

U.S. PATENT DOCUMENTS

| | | | |
|---|---|---|---|
| 4,453,005 | 6/1984 | Belanger et al. | 549/229 |
| 4,554,358 | 11/1985 | Takebe et al. | 549/229 |
| 4,587,258 | 5/1986 | Gold et al. | 514/412 |
| 4,654,331 | 3/1987 | Christensen | 549/229 |
| 4,822,803 | 4/1989 | Atkinson et al. | 514/463 |
| 4,849,524 | 7/1989 | Henning et al. | 548/411 |
| 4,868,307 | 9/1989 | Barton et al. | 546/256 |
| 4,886,827 | 12/1989 | Urbach et al. | 514/412 |

FOREIGN PATENT DOCUMENTS

| | | |
|---|---|---|
| 0079022 | 5/1983 | European Pat. Off. . |
| 0243645 | 11/1987 | European Pat. Off. . |
| 59-70683 | 4/1984 | Japan . |
| 87/2230 | 10/1987 | South Africa . |

OTHER PUBLICATIONS

U. Schindler et al., Nootropic Drugs: Animal Models for Studying Effects on Cognition, Drug Development Research 4:567-576 (1984).

R. T. Bartus, et al., Logical Principles for the Development of Animal Models of Age-Related Memory Impairments, Assessment in Geriafric Psychopharmacology, published by Mark Pauley Associates, Inc. 88 Main St., New Cannan, CT, USA. Dec. 1983, pp. 263-299.

G. Pepeu, The Relationship Between the Behavioral Effects of Cognition-Enhancing Drug and Brain Acetylcholine, Pharmacopsychiat, 22, 116-119, (1989).

N. Irving Sax and Richard J. Lewis, Sr., Hawley's Condensed Chemical Dictionary, 11th ed., p. 54.

*Primary Examiner*—C. Warren Ivy
*Assistant Examiner*—Ba K. Trinh
*Attorney, Agent, or Firm*—Finnegan, Henderson, Farabow, Garrett and Dunner

[57] ABSTRACT

New amino acid esters, a process for their preparation, medicaments containing them, and the use thereof The invention relates to amino acid esters of the formula I

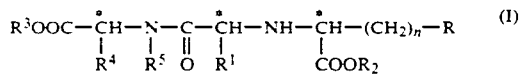

in which n is 1 or 2, R, $R^1$, $R^2$ and $R^3$ denote hydrogen or a defined radical, $R^4$ together with $R^5$ and the atoms carrying them form a heterocyclic ring system, to a process for their preparation, to agents containing them, and to the use thereof.

4 Claims, No Drawings

NEW AMINO ACID ESTERS, A PROCESS FOR THEIR PREPARATION, MEDICAMENTS CONTAINING THEM, AND THE USE THEREOF

This is a continuation of application Ser. No. 07/244,389, filed Sep. 14, 1988, now abandoned.

The invention relates to amino acid esters of the formula I

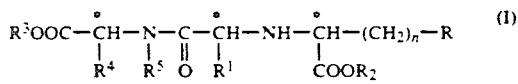

in which
N is 1 or 2,
R denotes hydrogen,
  an optionally substituted aliphatic radical having 1-21 carbon atoms,
  an optionally substituted alicyclic radical having 3-20 carbon atoms,
  an optionally substituted aromatic radical having 6-12 carbon atoms,
  an optionally substituted araliphatic radical having 7-32 carbon atoms,
  an optionally substituted alicyclic-aliphatic radical having 7-14 carbon atoms,
  an optionally substituted heteroaromatic or heteroaromatic-($C_1$-$C_8$)-aliphatic radical having 5-12 ring atoms, or
  a radical $OR^a$ or $SR^a$, in which
    $R^a$ stands for an optionally substituted aliphatic radical having 1-4 carbon atoms, for an optionally substituted aromatic radical having 6-12 carbon atoms, or an optionally substituted heteroaromatic radical having 5-12 ring atoms,
$R^1$ denotes hydrogen,
  an optionally substituted aliphatic radical having 1-21 carbon atoms,
  an optionally substituted alicyclic radical having 3-20 carbon atoms,
  an optionally substituted alicyclic-aliphatic radical having 4-20 carbon atoms,
  an optionally substituted aromatic radical having 6-12 carbon atoms,
  an optionally substituted araliphatic radical having 7-32 carbon atoms,
  an optionally substituted heteroaromatic or heteroaromatic-($C_1$-$C_8$)-aliphatic radical having 5-12 ring atoms or,
  if not already encompassed by the preceding definitions, the side chain, which is protected if necessary, of a naturally occurring α-amino acid,
$R^2$ and $R^3$ are identical or different and denote hydrogen, an optionally substituted aliphatic radical having 1-21 carbon atoms,
  an optionally substituted alicyclic radical having 3-20 carbon atoms,
  an optionally substituted aromatic radical having 6-12 carbon atoms,
  an optionally substituted araliphatic radical having 7-32 carbon atoms,
  a radical of the formula

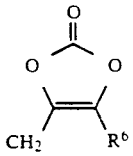

in which $R^6$ is hydrogen, an aliphatic radical having 1-6 carbon atoms or an optionally substituted aromatic radical having 6-12 carbon atoms,
  where
    at least one of the radicals $R^2$ or $R^3$ denotes a radical of the formula

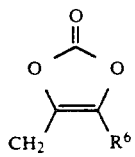

and
  $R^4$ and $R^5$ form, together with the atoms carrying them, a bi- or tricyclic heterocyclic ring system having 5 to 15 ring carbon atoms,
and to the physiologically tolerated salts thereof with acids and bases.

An optionally substituted aliphatic radical is defined as an aliphatic acyclic radical, i.e. a radical having an open, straight or branched carbon chain, such as, for example, alkyl, alkenyl, alkynyl and corresponding multiply unsaturated radicals. It is unsubstituted or monosubstituted as described below for example for carboxyl, carbamoyl, aminoalkyl, alkanoylaminoalkyl, alkoxycarbonylaminoalkyl, arylalkoxycarbonylaminoalkyl, arylalkylaminoalkyl, alkylaminoalkyl, dialkylaminoalkyl, alkylthioalkyl, arylthioalkyl, carboxyalkyl, carbamoylalkyl, alkoxycarbonylalkyl, alkanoyloxyalkyl, alkoxycarbonyloxyalkyl, aroyloxyalkyl or aryloxycarbonyloxyalkyl, preferably $C_1$-$C_5$)-alkanoyloxy-($C_1$-$C_8$)alkyl, in particular acetoxymethyl, propionyloxymethyl, isopropionyloxymethyl, n-butyryloxymethyl, pivaloyloxymethyl, isovaleroyloxymethyl, 1-acetoxyethyl, 1-n-propionyloxyethyl, 1-acetoxypropyl, or ($C_1$-$C_6$)-alkoxycarbonyloxy-($C_1$-$C_8$)-alkyl, in particular 1-methoxycarbonyloxyethyl, 1-ethoxycarbonyloxyethyl, 1-isopropoxycarbonyloxyethyl, 1-(cyclohexyloxycarbonyloxy)-ethyl, methoxycarbonyloxymethyl.

An optionally substituted alicyclic radical, and the corresponding alicyclic-aliphatic radical which is optionally substituted and which is bond via an open carbon chain, is a preferably mono- to pentacyclic isocyclic non-aromatic radical which has single bonds or unsymmetrically distributed double bonds and which can also be branched (i.e. can carry open-chain aliphatic side chains) and which is linked via a ring carbon atom or a side-chain carbon atom. It is preferably unsubstituted. Several rings as components of a radical of this type are condensed, spiro-linked or isolated. Examples of radicals of this type are cycloalkyl, cycloalkenyl, cycloalkylalkyl, bicycloalkyl, tricycloalkyl and radicals derived from mono-, bi or oligocyclic terpenes, such as menthyl, isomenthyl, bornyl, caranyl, epibornyl, epiisobornyl, isobornyl, norbornyl, neomenthyl, neoisomenthyl, pinanyl and thujanyl; they are preferably unsubstituted (aliphatic side chains are not substituents according to the present definition).

An optionally substituted aromatic radical is preferably aryl such as phenyl, biphenylyl or naphthyl, which is optionally mono-, di- or trisubstituted as indicated below for aryl. Radicals derived from aryl, such aralkyl, aryloxy, arylthio or aroyl, preferably benzoyl, can be substituted as aryl.

An optionally substituted heteroaromatic radical is preferably an aromatic mono- or bicyclic heterocyclic radical having 5 to 7 or 8 to 12, respectively, preferably up to 10, ring atoms, 1 or 2 of these ring atoms being sulfur or oxygen atoms and/or 1 to 4 of these ring atoms being nitrogen atoms, such as, for example, thienyl, benzo[b]thienyl, furyl, pyranyl, benzofuryl, pyrrolyl, imidazolyl, pyrazolyl, pyridyl, pyrimidinyl, pyridazinyl, indazolyl, isoindolyl, indolyl, purinyl, quinolizinyl, isoquinolinyl, phthalazinyl, naphthyridinyl, quinoxalinyl, quinazolyl, cinnolinyl, pteridinyl, oxazolyl, isoxazolyl, thiazolyl or isothiazolyl. These radicals can also be partially or completely hydrogenated. A heteroaromatic radical and the corresponding heteroaromatic-aliphatic radical can be substituted as defined below.

An optionally substituted araliphatic radical is to be understood to be, in particular, phthalidyl and arylalkyl, diarylalkyl, indanyl or fluorenyl, in which aryl is as defined above and can be substituted in the manner indicated there.

$R^4$ and $R^5$ can, together with the atoms carrying them, form a mono-, bi- or tricyclic heterocyclic ring system which has 3 to 15 ring carbon atoms and which has in the ring preferably up to 2 sulfur atoms and up to 2 nitrogen atoms, in particular up to 1 sulfur atom.

Particularly suitable ring systems of these types are those from the following group:

tetrahydroisoquinoline (A); decahydroisoquinoline (B); octahydroindole (C); octahydrocyclopenta[b]pyrrole (D); 2-azaspiro[4.5]decane (E); 2-azaspiro[4.4]nonane (F); spiro[bicyclo[2.2.1]heptane-2,3'-pyrrolidine] (G); spiro[bicyclo[2.2.2]octane-2,3'-pyrrolidine] (H); 2-azatricyclo[4.3.0.1$^{6,9}$]decane (I); decahydrocyclohepta[b]-pyrrole (J); hexahydrocyclopropa[b]pyrrole (K); octahydroisoindole (L); octahydrocyclopenta[c]pyrrole (M); 2,3,3a,4,5,7a-hexahydroindole (N); 1,2,3,3a,4,6a-hexahydrocyclopenta[b]pyrrole (O); all of which can optionally be substituted.

Tetrahydroisoquinoline (A) can carry, for example, in the aryl moiety up to 2 ($C_1$-$C_6$)-alkoxy radicals, preferably methoxy radicals. A corresponding statement applies to the other ring systems. However, the unsubstituted systems are preferred.

The suitable cyclic amino acid esters have the following structural formulae:

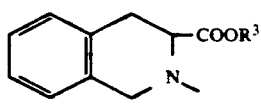

A

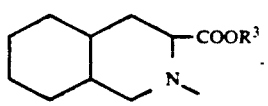

B

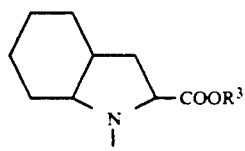

C

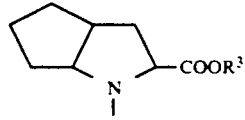

D

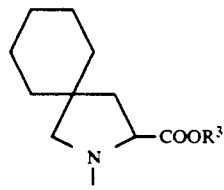

E

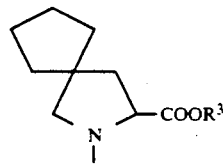

F

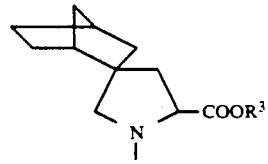

G

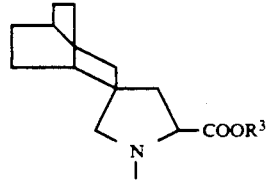

H

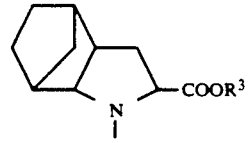

I

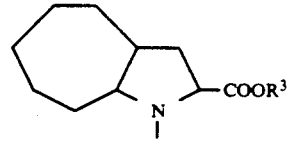

J

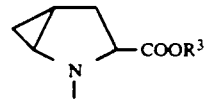

K

L

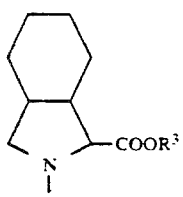

M

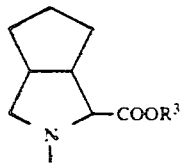

N

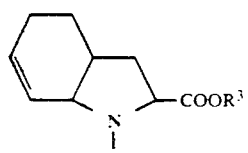

O

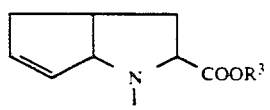

Particularly preferrred ring systems are A, C, D and H in which the carbon atom carrying the COOR$^3$ group preferably has the S configuration.

Examples of naturally occurring α-amino acids are Ala, Ser, Thr, Val, Leu, Ile, Asp, Asn, Glu, Gln, Arg, Lys, Hyl, Orn, Cit, Tyr, Phe, Trp and His.

If R$^1$ represents a side chain of a protected naturally occurring α-amino acid, such as, for example, protected Ser, Thr, Asp, Asn, Glu, Gln, Arg, Lys, Hyl, Cys, Orn, Cit, Tyr, Trp or His, the preferred protective groups are the groups customary in peptide chemistry (cf. Houben-Weyl, Vol. XV/1 and XV/2). In the case where R$^1$ denotes the protected lysine side chain, the known amino protective groups are preferred, but in particular Z, Boc or ($C_1$–$C_6$)-alkanoyl. Suitable and preferred as O-protective groups for tyrosine are ($C_1$–$C_6$)-alkyl, in particular methyl or ethyl.

The compounds of the formula I have asymmetric carbon atoms and can thus occur as enantiomers and diastereomers. The invention encompasses both the pure enantiomers and the racemates.

In the case of compounds which have several chiral atoms, all possible diastereomers as racemates or enantiomers, or mixtures of various diastereomers, are suitable. The racemates can be resolved by conventional methods, for example by salt formation with optically active acids such as camphorsulfonic acid or dibenzoyltartaric acid, fractional crystallization and subsequent liberation of the bases from their salts, or by derivatization with suitable optically active reagents, separation of the diastereomeric derivatives by fractional crystallization or chromatography on silica gel or alumina, and cleavage to return to the enantiomers. The diastereomers can be separated by conventional methods such as fractional crystallization of chromatography on columns.

Preferred compounds of the formula I are those in which a) n is 1 or 2
b) R
1. denotes hydrogen,
2. denotes alkyl having 1–18 carbon atoms,
3. denotes an aliphatic acyclic radical of the formula $C_aH_{(2a-b+1)}$ in which double bonds, if their number exceeds 1, are not cumulative, a represents an integer 2 to 18, and b represents an even number 2 to a;
4. denotes a mono-, di-, tri-, tetra- or pentacyclic non-aromatic hydrocarbon radical of the formula $C_cH_{(2c-d-1)}$ which is optionally branched and in which c represents an integer 3 to 20, and d represents an even number 0 to (c−2);
5. denotes aryl which has 6–12 carbon atoms and which can be mono-, di- or trisubstituted by ($C_1$–$C_8$)-alkyl, ($C_1$–$C_4$)-alkoxy, hydroxyl, halogen, nitro, amino, aminomethyl, ($C_1$–$C_4$)-alkylamino, di-($C_1$–$C_4$)-alkylamino, ($C_1$–$C_4$)-alkanoylamino, methylenedioxy, carboxyl, cyano and/or sulfamoyl;
6. if n is 2, denotes ($C_6$–$C_{12}$)-aryl-($C_1$–$C_8$)-alkyl or di-($C_6$–$C_{12}$)-aryl-($C_1$–$C_8$)-alkyl, each of which can be substituted in the aryl moiety as described under b) 5.; or denotes
7. alkoxy having 1–4 carbon atoms;
8. aryloxy which has 6–12 carbon atoms and can be substituted as described under b) 5.;
9. mono- or bicyclic heteroaryloxy or heteroaryl-($C_1$–$C_8$)-alkyl having 5–7 or 8–10, respectively, ring atoms, up to 9 of these ring atoms being carbon and 1 or 2 ring atoms being sulfur or oxygen and/or 1 to 4 ring atoms being nitrogen, each of which can be substituted in the heteroaryl as described under b) 5.;
10. amin-($C_1$–$C_8$)-alkyl;
11. ($C_1$–$C_4$)-alkanoylamino-($C_1$–$C_8$)-alkyl; '12. ($C_7$–$C_{13}$)-aroylamino-($C_1$–$C_8$)-alkyl;
13. ($C_1$–$C_4$)-alkoxycarbonylamino-($C_1$–$C_8$)-alkyl;
14. ($C_6$–$C_{12}$)-aryl-($C_1$–$C_4$)-alkoxycarbonylamino-($C_1$–$C_8$)-alkyl;
15. ($C_6$–$C_{12}$)-aryl-($C_1$–$C_4$)-alkylamino-($C_1$–$C_8$)-alkyl;
16. ($C_1$–$C_4$)-alkylamino-($C_1$–$C_8$)alkyl;
17. di-($C_1$–$C_4$)-alkylamino-($C_1$–$C_8$)-alkyl;
18. guanidino-($C_1$–$C_8$)-alkyl;
19. imidazolyl;
20. indolyl;
21. ($C_1$–$C_4$)-alkylthio;
22. if n is 2, ($C_1$–$C_4$)-alkylthio-($C_1$–$C_8$)alkyl;
23. ($C_6$–$C_{12}$)-arylthio-($C_1$–$C_8$)-alkyl which can be substituted in the aryl moiety as described under b) 5.;
24. ($C_6$–$C_{12}$)-aryl-($C_1$–$C_8$)-alkylthio which can be substituted in the aryl moiety as described under b) 5.;
25. if n is 2, carboxy-($C_1$–$C_8$)-alkyl;
26. carboxyl;
27. carbamoyl;
28. if n is 2, carbamoyl-($C_1$–$C_8$)-alkyl;
29. ($C_1$–$C_4$)-alkoxycarbonyl-($C_1$–$C_8$)-alkyl;
30. if n is 2, ($C_6$–$C_{12}$)-aryloxy-($C_1$–$C_8$)-alkyl which can be substituted in the aryl moiety as described under b) 5.; or 31. $(C_6-C_{12})$-aryl-$(C_1-C_8)$-alkoxy which can be substituted in the aryl moiety as described under b) 5.;

c) $R^1$
1. denotes hydrogen;
2. denotes alkyl having 1-18 carbon atoms;
3. denotes an aliphatic acyclic radical of the formula $C_aH_{(2a-b+1)}$ in which double bonds, if their number exceeds 1, are not cumulative, a represents an integer 2 to 18, and b represents an even number 2 to a;
4. denotes a mono-, di-, tri-, tetra- or pentacyclic non-aromatic hydrocarbon radical of the formula $C_cH_{(2c-d-1)}$ which is optionally branched and in which c represents an integer 3 to 20, and d represents an even number 0 to (c−2);
5. aryl which has 6-12 carbon atoms and can be substituted as described under b) 5.;
6. $(C_6-C_{12})$-aryl-$(C_1-C_8)$-alkyl or $(C_7-C_{13})$-aroyl-$(C_1-C_8)$-alkyl, both of which can be substituted as aryl described under b) 5.;
7. mono- or bicyclic, optionally partially hydrogenated heteroaryl or heteroaryl-$(C_1-C_8)$-alkyl having 5-7 or 8-10 ring atoms, respectively, up to 9 of these ring atoms being carbon and 1 or 2 ring atoms being sulfur or oxygen atoms and/or 1 to 4 ring atoms being nitrogen atoms, each of which can be substituted in the heteroaryl as described for aryl under b) 5.; or
8. if not yet encompassed by c) 1.-7., denotes the optionally protected side chain of a naturally occurring α-amino acid of the formula $R^1-CH(NH_2)-COOH$;

d) $R^2$ and $R^3$ are identical or different and
1. denote hydrogen;
2. denote alkyl having 1-18 carbon atoms;
3. denote an aliphatic acyclic radical of the formula $C_aH_{(2a-b+1)}$ in which double bonds, if their number exceeds 1, are not cumulative, a represents an integer 2 to 18, and b represents an even number 2 to a;
4. denote a mono-, di-, tri-, tetra- or pentacyclic non-aromatic hydrocarbon radical of the formula $C_cH_{(2c-d-1)}$ which is optionally branched and in which c represents an integer 3 to 20, and d represents an even number 0 to (c−2);
5. di-$(C_1-C_4)$-alkylamino-$(C_1-C_8)$-alkyl;
6. $(C_1-C_5)$-alkanoyloxy-$(C_1-C_8)$-alkyl;
7. $(C_1-C_6)$alkoxycarbonyloxy-$(C_1-C_8)$-alkyl;
8. $(C_7-C_{13})$-aroyloxy-$(C_1-C_8)$-alkyl;
9. $(C_6-C_{12})$-aryloxycarbonyloxy-$(C_1-C_8)$-alkyl;
10. aryl having 6-12 carbon atoms;
11. $(C_7-C_{20})$-aralkyl;
12. phthalidyl; or
13. denote a radical of the formula

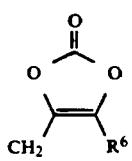

in which $R^6$ is hydrogen, $(C_1-C_6)$-alkyl or aryl having 6-12 carbon atoms, it being possible for the radicals mentioned under d) 8., 9., 10., 11. and 12. to be substituted in the aryl moiety as described under b) 5.; and where at least one of the radicals $R^2$ or $R^3$ denotes a radical of the formula

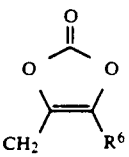

and e) $R^4$ and $R^5$ form, together with the atoms carrying them, a bi- or tricyclic heterocyclic ring system having 5 to 15 ring carbon atoms;

as well as the physiologically tolerated salts thereof with acids and bases.

Particularly preferred compounds of the formula I are those in which n is 1 or 2, R denotes hydrogen,
alkyl having 1-8 carbon atoms,
alkenyl having 2-6 carbon atoms,
cycloalkyl having 3-9 carbon atoms and can be mono-, di- or trisubstituted by $(C_1-C_4)$-alkyl, $(C_1-C_4)$-alkoxy, hydroxyl, halogen, nitro, amino, aminomethyl, $(C_1-C_4)$-alkylamino, di-$(C_1-C_4)$-alkylamino, $(C_1-C_4)$-alkanoylamino, methylenedioxy, carboxyl, cyano and/or sulfamoyl,
alkoxy having 1-4 carbon atoms,
aryloxy which has 6-12 carbon atoms and can be substituted as described above for aryl,
mono- or bicyclic heteroaryloxy having 5-7 or 8-10 ring atoms, respectively, 1 or 2 of these ring atoms being sulfur or oxygen atoms and/or 1 to 4 ring atoms being nitrogen, which can be substituted as described above for aryl,
amino-$(C_1-C_4)$-alkyl,
$(C_1-C_4)$-alkanoylamino-$(C_1-C_4)$-alkyl,
$(C_7-C_{13})$-aroylamino-$(C_1-C_4)$-alkyl,
$(C_1-C_4)$-alkoxycarbonylamino-$(C_1-C_4)$alkyl,
$(C_6-C_{12})$-aryl-$(C_1-C_4)$-alkoxycarbonylamino-$(C_1-C_4)$-alkyl,
$(C_6-C_{12})$-aryl-$(C_1-C_4)$-alkylamino-$(C_1-C_4)$-alkyl,
$(C_1-C_4)$-alkylamino-$(C_1-C_4)$-alkyl,
di-$(C_1-C_4)$-alkylamino-$(C_1-C_4)$-alkyl,
guanidino-$(C_1-C_4)$-alkyl,
imidazolyl, indolyl,
$(C_1-C_4)$-alkylthio,
$(C_1-C_4)$-alkylthio-$(C_1-C_4)$-alkyl,
$(C_6-C_{12})$-arylthio-$(C_1-C_4)$-alkyl which can be substituted in the aryl moiety as described above for aryl
$(C_6-C_{12})$-aryl-$(C_1-C_4)$-alkylthio which can be substituted in the aryl moiety as described above for aryl,
carboxy-$(C_1-C_4)$-alkyl,
carboxyl, carbamoyl,
carbamoyl-$(C_1-C_4)$-alkyl,
$(C_1-C_4)$-alkoxycarbonyl-$(C_1-C_4)$-alkyl,
$(C_6-C_{12})$aryloxy-$(C_1-C_4)$-alkyl which can be substituted in the aryl moiety as described above for aryl, or
$(C_6-C_{12})$-aryl-$(C_1-C_4)$-alkoxy which can be substituted in the aryl moiety as described above for aryl, $R^1$ denotes hydrogen
alkyl having 1-6 carbon atoms, alkenyl having 2-6 carbon atoms,
alkynyl having 2-6 carbon atoms,
cycloalkyl having 3-9 carbon atoms,
cycloalkenyl having 5-9 carbon atoms,
$(C_3-C_9)$-cycloalkyl-$(C_1-C_4)$-alkyl,
$(C_5-C_9)$-cycloalkenyl-$(C_1-C_4)$-alkyl,
optionally partially hydrogenated aryl which has 6-12 carbon atoms and can be substituted as described above for R,
$(C_6-C_{12})$-aryl-$(C_1-C_4)$alkyl or $(C_7-C_{13})$-aroyl-$(C_1$ or $C_2)$-alkyl, both of which can be substituted as the preceding aryl,
mono- or bicyclic, optionally partially hydrogenated heteroaryl having 5-7 or 8-10 ring atoms, respectively, 1 or 2 of these ring atoms being sulfur or oxygen atoms and/or 1 to 4 ring atoms being nitrogen atoms, which can be substituted as the preceding aryl, or the optionally protected side chain of a naturally occurring α-amino acid $R^1$—CH(NH$_2$)—COOH, $R^2$ and $R^3$ are identical or different and denote hydrogen,
alkyl having 1-6 carbon atoms,
alkenyl having 2-6 carbon atoms,
di-$(C_1-C_4)$-alkylamino-$(C_1-C_4)$-alkyl,
$(C_1-C_5)$-alkanoyloxy-$(C_1-C_4)$-alkyl,
$(C_1-C_6)$-alkoxycarbonyloxy-$(C_1-C_4)$-alkyl,
$(C_7-C_{13})$-aroyloxy-$(C_1-C_4)$-alkyl,
$(C_6-C_{12})$-aryloxycarbonyloxy-$(C_1-C_4)$-alkyl,
aryl having 6-12 carbon atoms,
$(C_6-C_{12})$-aryl-$(C_1-C_4)$-alkyl,
$(C_3-C_9)$-cycloalkyl,
$(C_3-C_9)$-cycloalkyl-$(C_1-C_4)$-alkyl,
phthalidyl or
a radical of the formula

in which $R^6$ is hydrogen, $(C_1-C_6)$-alkyl or aryl having 6-12 carbon atoms, and where at least one of the radicals $R^2$ or $R^3$ denotes a radical of the formula

and
$R^4$ and $R^5$ have the meaning indicated above, as well as the physiologically tolerated salts thereof with acids and bases.

Very particularly preferred compounds of the formula I are those in which
n is 1 or 2;
R denotes $(C_1-C_6)$-alkyl, $(C_2-C_6)$-alkenyl, $(C_3-C_9)$-cycloalkyl, amino-$(C_1-C_4)$-alkyl, $(C_2-C_5)$-acylamino-$(C_1-C_4)$-alkyl, $(C_7-C_{13})$-aroylamino-$(C_1-C_4)$-alkyl, $(C_1-C_4)$-alkoxycarbonylamino-$(C_1-C_4)$-alkyl, $(C_6-C_{12})$-aryl-$(C_1-C_4)$-alkoxycarbonylamino-$(C_1-C_4)$-alkyl, $(C_6-C_{12})$-aryl which can be mono-, di- or trisubstituted by $(C_1-C_4)$-alkyl, $(C_1-C_4)$-alkoxy, hydroxyl, halogen, nitro, amino, $(C_1-C_4)$-alkylamino, di-$(C_1-C_4)$-alkylamino and/or methylenedioxy, or 3-indolyl, in particular methyl, ethyl, cyclohexyl, tert.-butoxycarbonylamino-$(C_1-C_4)$-alkyl, benzyloxycarbonylamino-$(C_1-C_4)$-alkyl, or phenyl which can be mono- or disubstituted, or in the case of methoxy trisubstituted, by phenyl, $(C_1-C_2)$-alkyl, $(C_1$ or $C_2)$-alkoxy, hydroxyl, fluorine, chlorine, bromine, amino, $(C_1-C_4)$-alkylamino, di-$(C_1-C_4)$-alkylamino, nitro and/or methylenedioxy, $R^1$ denotes hydrogen or $(C_1-C_6)$-alkyl which can optionally be substituted by amino, $(C_1-C_6)$-acylamino or benzoylamino, or denotes $(C_2-C_6)$-alkenyl, $(C_3-C_9)$-cycloalkyl, $(C_5-C_9)$-cycloalkenyl, $(C_3-C_7)$-cycloalkyl-$(C_1-C_4)$-alkyl, $(C_6-C_{12})$-aryl or partially hydrogenated aryl, each of which can be substituted by $(C_1-C_4)$-alkyl, $(C_1$ or $C_2)$-alkoxy or halogen, or denotes $(C_6-C_{12})$ aryl-$(C_1$ to $C_4)$-alkyl or $(C_7-C_{13})$-aroyl-$(C_1-C_2)$-alkyl, both of which can be substituted in the aryl radical as defined above, or denotes a mono- or bicyclic heterocyclic radical having 5 to 7 or 8 to 10 ring atoms, respectively, 1 or 2 of these ring atoms being sulfur or oxygen atoms and/or 1 to 4 ring atoms being nitrogen atoms, or a side chain of a naturally occurring optionally protected α-amino acid, but in particular hydrogen, $(C_1-C_3)$-alkyl, $(C_2$ or $C_3)$-alkenyl, the optionally protected side chain of lysine, phenylalanine or tyrosine, benzyl, 4-methoxybenzyl, 4-ethoxybenzyl, phenethyl, 4-aminobutyl or benzoylmethyl, $R^2$ and $R^3$ denote identical or different radicals hydrogen, $(C_1-C_6)$-alkyl, $(C_2-C_6)$-alkenyl, $(C_6-C_{12})$-aryl-$(C_1-C_4$-alkyl, $(C_1-C_5)$-alkanoyloxy-$(C_1-C_4)$-alkyl, $(C_1-C_6)$-alkoxycarbonyloxy-$(C_1-C_4)$-alkyl, $(C_7-C_{13})$-aroyloxy-$(C_1-C_4)$-alkyl, $(C_6-C_{12})$-aryloxycarbonyloxy-$(C_1-C_4)$-alkyl, phthalidyl or a radical of the formula

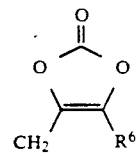

in which $R^6$ is hydrogen, $(C_1-C_6)$-alkyl or aryl having 6-12 carbon atoms, where at least one of the radicals $R^2$ or $R^3$ denotes a radical of the formula

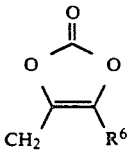

but in particular hydrogen, $(C_1-C_4)$-alkyl, benzyl, acetoxymethyl, propionyloxymethyl, isopropionyloxymethyl, n-butyryloxymethyl, pivaloyloxymethyl, isovaleroyloxymethyl, 1-acetoxyethyl, 1-(n-propionyloxy)-ethyl, 1-acetoxypropyl, 1-(methoxycarbonyloxy)ethyl, 1-(ethoxycarbonyloxy)ethyl, 1-(isopropoxycarbonyloxy)-ethyl, 1-(cyclohexyloxycarbonyloxy)ethyl, methoxycarbonyloxymethyl, phthalidyl, (5-methyl-1,3-dioxolen-2-on-4-yl)methyl, (5-tert. butyl-1,3-dioxolen-2-on-4-yl)-methyl or (5-phenyl-1,3-dioxolen-2-on-4-yl)methyl and $R^4$ and $R^5$ have the meaning indicated above, as well as the physiologically tolerated salts thereof with acids and bases.

Examples of very particularly preferred compounds are:

5-methyl-1,3-dioxolen-2-on-4-ylmethyl 2-[N-(1S-ethoxycarbonyl-3-phenylpropyl)-S-alanyl]-(1S,3S,5S)-2-azabicyclo-[3.3.0]octane-3-carboxylate;

5-methyl-1,3-dioxolen-2-on-4-ylmethyl 2-[N-(1S-carboxy-3-phenylpropyl)-S-alanyl]-(1S,3S,5S)-2-azabicyclo-[3.3.0]octane-3-carboxylate;

5-methyl-1,3-dioxolen-2-on-4-ylmethyl 2-[N-[1S-[5-methyl-1,3-dioxolen-2-on-4-ylmethoxycarbonyl]-3-phenylpropyl]-S-alanyl]-(1S,3S,5S)-2-azabicyclo[3.3.0]octane-3-carboxylate;

benzyl 2-[N-[1S-[5-methyl-1,3-dioxolen-2-on-4-ylmethoxycarbonyl]-3-phenylpropyl]-S-alanyl]-(1S,3S,5S)-2-azabicyclo[3.3.0]octane-3-carboxylate;

octyl 2-[N-[1S-[5-methyl-1,3-dioxolen-2-on-4-ylmethoxycarbonyl]-3-phenylpropyl]-S-alanyl]-(1S,3S,5S-2-azabicyclo[3.3.0]octane-3-carboxylate;

2-[N-[1S-[5-methyl-1,3-dioxolen-2-on-4-ylmethoxycarbonyl]-3-phenylpropyl]-S-alanyl]-(1S,3S,5)-2-azabicyclo[3.3.0]-octane-3-carboxylic acid;

5-methyl-1,3-dioxolen-2-on-4-ylmethyl 1-[N-(1S-ethoxycarbonyl-3-phenylpropyl)-S-alanyl]-(2S,3aR,7aS)-octahydro[1H]indole-2-carboxylate;

5-methyl-1,3-dioxolen-2-on-4-ylmethyl 1-[N-(1S-carboxy-3-phenylpropyl)-S-alanyl]-(2S,3aR,7aS)-octahydro[1H]indole-2-carboxylate;

5-methyl-1,3-dioxolen-2-on-4-ylmethyl 1-[N-[1S-[5-methyl-1,3-dioxolen-2-on-4-ylmethoxycarbonyl]-3-phenylpropyl]-S-alanyl]-(2S,3aR,7aS)-octahydro[1H]indole-2-carboxylate;

benzyl 1-[N-[1S-[5-methyl-1,3-dioxolen-2-on-4-ylmethoxycarbonyl]-3-phenylpropyl]-S-alanyl]-(2S,3aR,7aS)-octahydro[1H]indole-2-carboxylate;

octyl 1-[N-[1S-[5-methyl-1,3-dioxolen-2-on-4-ylmethoxycarbonyl]-3-phenylpropyl]-S-alanyl]-(2S,3aR,7aS)-octahydro[1H]indole-2-carboxylate;

1-[N-[1S-[5-methyl-1,3-dioxolen-2-on-4-ylmethoxycarbonyl]-3-phenylpropyl]-S-alanyl]-(2S,3aR,7aS)-octahydro[1H]indole- 2-carboxylic acid;

benzhydryl 1-[N-[1S-[5-methyl-1,3-dioxolen-2-on-4-yl-methoxycarbonyl]-3-phenylpropyl]-S-alanyl]-(2S,3aR,7aS)-octahydro[1H]indole-2-carboxylate;

5-methyl-1,3-dioxolen-2-on-4-ylmethyl 2-[N-(1S-ethoxycarbonyl-3-phenylpropyl)-S-alanyl]-1,2,3,4-tetrahydroisoquinoline-3S-carboxylate;

5-methyl-1,3-dioxolen-2-on-4-ylmethyl 2-[N-(1S-carboxy-3-phenylpropyl)-S-alanyl]-1,2,3,4-tetrahyroisoquinoline-3S-carboxylate;

5-methyl-1,3-dioxolen-2-on-4-ylmethyl 2-[N-[1S-[5-methyl-1,3-dioxolen-2-on-4-ylmethoxycarbonyl]-3-phenylpropyl]-S-alanyl]-1,2,3,4-tetrahydroisoquinoline-3S-carboxylate;

benzyl 2-[N-[1S-[5-methyl-1,3-dioxolen-2-on4-ylmethoxycarbonyl]-3-phenylpropyl]-S-alanyl]-1,2,3,4-tetrahydroisoquinoline-3S-carboxylate;

2-[N-[1S-[5-methyl-1,3-dioxolen-2-on-4-ylmethoxycarbonyl]-3-phenylpropyl]-S-alanyl]-1,2,3,4-tetrahydroisoquinoline-3S-carboxylic acid;

octyl 2-[N-[1S-[5-methyl-1,3-dioxolen-2-on-4-ylmethoxycarbonyl]-3-phenylpropyl]-S-alanyl]-1,2,3,4-tetrahydroisoquinoline-3S-carboxylate;

5-methyl-1,3-dioxolen-2-on-4-ylmethyl 1-[N-(1S-ethoxycarbonyl-3-phenylpropyl)-S-alanyl]-3'S-spiro[bicyclo-[2.2.2]octane-2,3'-pyrrolidin]-5'S-ylcarboxylate;

5-methyl-1,3-dioxolen-2-on-4-ylmethyl 1-[N-(1S-carboxy-3-phenylpropyl)-S-alanyl]-3'S-spiro[bicyclo[2.2.2]octane-2,3'-pyrrolidin]-5'S-ylcarboxylate;

5methyl-1,3-dioxolen-2-on-4-ylmethyl 1-[N-[1S-[5-methyl-1,3-dioxolen-2-on-4-ylmethoxycarbonyl]-3-phenylpropyl]-S-alanyl]-3'S-spiro[bicyclo[2.2.2]octane-2,3'-pyrrolidin]-5'S-ylcarboxylate;

benzyl 1-[N-[1S-[5-methyl-1,3-dioxolen-2-on-4-ylmethoxycarbonyl]-3-phenylpropyl]-S-alanyl]-3'S-spiro[bicyclo[2.2.2]octane-2,3'-pyrrolidin]-5'S-ylcarboxylate;

1-[N-[1S-[5-methyl-1,3-dioxolen-2-on-4-ylmethoxycarbonyl[-3-phenylpropyl]-S-alanyl]-3'S-spiro[bicyclo-[2.2.2]octane-2,3'-pyrrolidin]-5'S-ylcarboxylate;

5-methyl-1,3-dioxolen-2-on-4-ylmethyl 1-[N-(1S-ethoxycarbonylbutyl)-S-alanyl]-(2S,eaS,7aS)-octahydro[1H]indole-2-carboxylate 5-methyl-1,3-dioxolen-2-on-4-ylmethyl 1-[N-(1S-carboxybutyl)-S-alanyl]-(2S,3aS,7aS)-octahydro[1H]indole-2-carboxylate 5-methyl-1,3-dioxolen-2-on-4-ylmethyl 1-[N-[1S-[5-methyl-1,3-dioxolen-2-on-4-ylmethoxycarbonyl]-butyl]-S-alanyl]-(2S,3aS,7aS)-octahydro[1H]indole-2-carboxylate;

benzyl 1-[N-[1S-[5-methyl-1,3-dioxolen-2-on-4-ylmethoxycarbonyl]butyl]-S-alanyl]-(2S,3aS,7aS)-octahydro[1H]-indole-2-carboxylate;

1[N-[1S-[5-methyl-1,3-dioxolen-2-on-4-ylmethoxycarbonyl]-carbonyl]butyl]-S-alanyl]-(2S,3aS,7aS)-octahydro[1H]-indole-2-carboxylate.

Suitable salts of the compounds of the formula I are, depending on the acidic or basic nature of these compounds, alkalimetal or alkaline earth metal salts or salts with physiologically tolerated amines or salts with inorganic or organic acids such as, for example HCL, HBr, $H_2SO_4$, maleic acid, fumaric acid, tartaric acid or citric acid.

The invention also relates to a process for the preparation of compounds of the formula I, which comprises a) reaction of a compound of the formula II

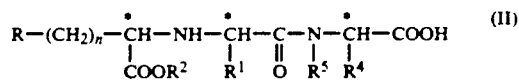

in which R, $R^1$, $R^2$, $R^4$, $R^5$ and n have the same meaning as in formula I, with a compound of the formula III

in which $R^6$ has the same meaning as in formula I, and in which X denotes a leaving group which can be displaced nucleophilically, in particular a chlorine, bromine or iodine atom or a sulfonic acid residue, preferably a bromine atom, under conditions of a nucleophilic substitution, preferably in a polar organic solvent such as an alcohol, preferably methanol, ethanol, propanol or isopropanol, preferably methanol, ethanol, propanol or isopropanol, or a lower ketone, preferably acetone, methyl ethyl, ketone or methyl isobutyl ketone, or in acetonitrile, dimethylformamide, dimethyl sulfoxide or sulfolane, or a hydrocarbon, preferably toluene, with or without the presence of an auxiliary base to capture the acid which is formed, preferably in the presence of potassium bicarbonate, potassium carbonate, sodium bicarbonate, sodium carbonate, triethylamine, pyridien, 1,8-diazabicyclo-[5.4.0]undec-7-ene or 1,5-diazabicyclo]4.3.0]non-5-ene, as well as with or without the presence of an alkali metal halide, preferably sodium iodide or potassium iodide, at a temperature between $-50°$ and $+100°$ C., preferably between $-20°$ and $+60°$ C., or comprises b) reaction of a compound of the formula IV

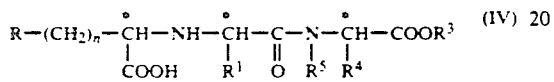

in which R, $R^1$, $R^3$, $R^4$, $R^5$ and n have the same meaning as in formula I, with a compound of the formula III as described under process variant a), or comprises c) reaction of a compound of the formula V

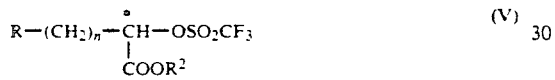

in which R, $R^2$ and n have the same meaning as in formula I, with a compound of the formula VI

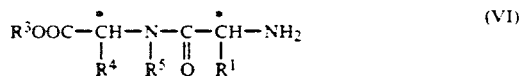

in which $R^1$, $R^3$, $R^4$ and $R^5$ have the same meaning as in formula I, for example in analogy to the procedure described in U.S. Pat. No. 4,525,301, or comprises d) reaction of a compound of the formula VI with a compound of the formula VII

in which R and $R^2$ have the same meaning as in formula I, in a known manner in a Michael reaction (Organikum, 6th edition, page 492, 1967), and hydrogenation of the carbonyl group, for example in acidic alcoholic solution with a noble metal catalyst, in particular palladium or platinum on active charcoal, under a pressure of 20 to 120 bar, or comprises e) reaction of a compound of the formula VI with a compound of the formula VIII

in which R, $R^2$ and n have the same meaning as in formula I, for example by the procedure described in J. Amer. Chem. Soc. 93, 2897 (1971), and reduction of the resulting Schiff bases, preferably using a complex hydride, for example sodium cyanoborohydride, and conversion, where appropriate, of the compounds of the formula I obtained in this way into their physiologically tolerated salts.

Compounds of the formula II and IV are known (see, for example, EP-A Nos. 79,022; 105,102; 113,880; 116,270; 84,164; 90,362).

Compounds of the formula III are known, for example from Chem. Pharm. Bull. 32, 2241 (1984) or are prepared by an analogous route from the appropriate starting materials.

Compounds of the formula V in which $R^2$ denotes the radical

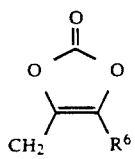

are obtained from compounds of the formula IX

in which R and n have the same meaning as in formula I, by reaction with compounds of the formula III under the conditions of a nucleophilic substitution as described under process variant a), and by subsequent conversion of the hydroxyl group into the $-OSO_2CF_3$ group by usual processes.

Compounds of the formula VI are dipeptides which can be synthesized from the individual amino acid components by methods of peptide chemistry which are known per se (see, for example, Houben-Weyl, Methoden der Organischen Chemie (Methods of Organic Chemistry) Vol. XV, Part II, pages 1-364).

Compounds of the formula VII in which $R^2$ denotes the radical

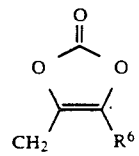

are obtained from compounds of the formula X

in which R has the same meaning as in formula I, by reaction with compounds of the formula III under the conditions of a nucleophilic substitution as described under process variant a).

Compounds of the formula VIII in which $R^2$ denotes the radical

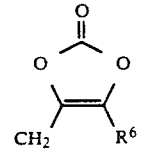

are obtained from compounds of the formula XI

in which R and n have the same meaning as in formula I, by reaction with compounds of the formula III under the conditions of a nucleophilic substitution as described under process variant a).

Compounds of the formulae IX, X and XI are known.

The invention also relates to new intermediates of the formula V

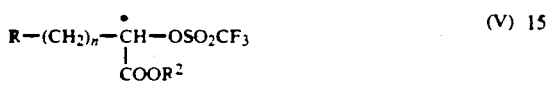

in which R and n have the same meaning as in formula I and in which $R^2$ denotes a radical of the formula

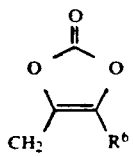

in which $R^6$ is hydrogen, an aliphatic radical having 1–6 carbon atoms or an optionally substituted aromatic radical having 6–12 carbon atoms.

The invention also relates to a process for the preparation of compounds of the formula V in which R and n have the same meaning as in formula I, and in which $R^2$ denotes a radical of the formula

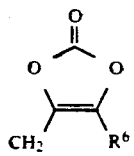

in which $R^6$ is hydrogen, an aliphatic radical having 1–6 carbon atoms or an optionally substituted aromatic radical having 6–12 carbon atoms, which comprises reaction of compounds of the formula IX

in which R and n have the same meaning as in formula I, with compounds of the formula III under the conditions of a nucleophilic substitution as described under process variant a), and subsequent conversion of the hydroxyl group into the $-OSO_2CF_3$ group by usual processes.

The compounds of the formula I are prodrug forms of inhibitors of angiotensin converting enzyme (ACE inhibitors). Compared with known ACE inhibitors, they have the advantage of increased absorbability and thus increased bioavailability. Under physiological conditions they are rapidly cleaved to the ACE inhibitors.

The compounds of the formula I and the salts thereof have a long-lasting and intense lowering action on blood pressure. They can be used to control high blood pressure of various estiologies. It is also possible to combine them with other compounds acting to lower blood pressure or dilate vessels or induce diuresis. Typical representatives of these active classes are described in, for example, Erhardt-Ruschig, Arzneimittel (Drugs), 2nd edition, Weinheim, 1972. Administration can be intravenous, subcutaneous or oral.

The dosage on oral administration is 1–100 mg, preferably 1–40 mg, per single dose for an adult patient of normal weight: this corresponds to about 15–1,300 μg/kg/day, preferably 15–500 μg/kg/day. It can also be increased in severe cases, because no toxic properties have hitherto been observed. It is also possible to reduce the dose, and this is particularly appropriate when diuretics are administered concurrently.

The compounds of the formula I according to the invention are, by reason of their pharmacological properties, suitable not only for the treatment of high blood pressure but also for the treatment of cognitive dysfunction of various etiologies as occur, for example, in Alzheimer's disease or in senile dementia. The nootropic action of the compounds according to the invention has been tested in mice, which had a body weight of 20–25 g, in the inhibitory (passive) avoidance test (step-through model). A modified form of the test method described by J. KOPP, Z. BODANECKY and M. E. JARVIK has been described by J. BURES. O. BURESOVA and J. HUSTON in "Techniques and Basic Experiments for the Study of Brain and Behavior", Elsevier Scientific Publishers, Amsterdam (1983).

According to these references, a substance is designated as having nootropic activity if it is able to abolish the amnesia generated by means of an electroconvulsive shock, or the amnesia induced by means of scopolamine, in the experimental animals.

The experiments were carried out using modified test methods. The comparison compound used was the known nootropic atent 2-oxo-1-pyrrolidinylacetamide (piracetam). The distinct superiority of the compounds according to the invention over the comparison substance was evident from the fact that the scopolamine-induced amnesia in the inhibitory avoidance test was abolished with an oral MED (minimal effective dose) of 0.03–30 mg/kg. The comparison substance had an oral MED of about 500–1,000 mg/kg.

Hence the invention also relates to the use of the compounds according to the invention for the treatment and prophylaxis of cognitive dysfunctions.

The invention also encompasses medicaments containing the said compounds, processes for the preparation thereof and the use of the compounds according to the invention for the preparation of medicaments which are used for the treatment and prophylaxis of the above-mentioned diseases.

Employing the method according to the invention, it is possible to use the angiotensin converting enzyme inhibitors described above on mammals such as monkeys, dogs, cats, rats, humans etc.

The medicaments are prepared in a manner which is known per se and is familiar to the expert. The pharmacologically active compounds (=active substance) according to the invention are used as medicaments either as such or, preferably, combined with suitable pharmaceutical auxiliaries in the form of tablets, coated tablets, capsules, suppositories, emulsifiers, suspensions or solutions, the content of active substance being up to about 95%, preferably between 10% and 75%.

The particular auxiliaries suitable for the desired medicament formulation are familiar to the expert on the basis of his expert knowledge. Beside solvents, gel-forming agents, suppository bases, tabletting auxiliaries and other active substance vehicles, it is possible to use, for example, antioxidants, dispersing agents, emulsifiers, antifoam agents, flavorings, preservatives, solubilizers or colorants.

The active substances can be administered, for example, orally, rectally or parenterally (for example intravenously or subcutaneously), with oral administration being preferred.

For a form for oral administration, the active compounds are mixed with the additives suitable for this purpose, such as vehicles, stabilizers or inert diluents, and converted by the customary methods into suitable dosage forms such as tablets, coated tablets, hard gelatin capsules, aqueous, alcoholic or oily suspensions or aqueous, alcoholic or oily solutions. Examples of inert vehicles which can be used are gum arabic, magnesia, magnesium carbonate, lactose, glucose or starch, especially corn starch. In this connection, the formulation can be carried out both as dry and as wet granules. Examples of suitable oily vehicles or solvents are vegetable or animal oils, such as sunflower oil or fish liver oil.

For subcutaneous or intravenous administration, the active compounds or their physiologically tolerated salts are converted, if desired with the substances customary for this purpose, such as solubilizers, emulsifiers or further auxiliaries, into a solution, suspension or emulsion. Examples of suitable solvents are water, physiological saline or alcohols, for example ethanol, propanol or glycerol, as well as sugar solutions such as glucose or mannitol solutions, or a mixture of the various solvents mentioned.

The examples which follow are intended to illustrate the compounds and process according to the invention without restricting the invention to the substances mentioned here as representative.

EXAMPLE 1

5-Methyl-1,3-dioxolen-2-on-4-ylmethyl 2-[N-(1S-ethoxycarbonyl-3-phenylpropyl)-S-alanyl]-(1S,3S,5S)-2-azabicyclo]3.3.0]octane-3-carboxylate;

1.36 g (13.6 mmol) of potassium bicarbonate are added to a solution of 2.82 g (7.66 mmol) of 2-[N-(1S-ethoxycarbonyl-3-phenylpropyl)-S-alanyl]-(1S,3S,5S)-2-azabicyclo-[3.3.0]octane-3-carboxylic acid (ramipril) in 25 ml of absolute dimethylformamide, and the mixture is stirred at 50° C. for 45 minutes. Then, while cooling in ice at 0° C., a solution of 1.57 g (8.13 mmol) of 4-bromomethyl-5-methyl-1,3-dioxolen-2-one in 7 ml of absolute dimethylformamide is added dropwise, and the mixture is then stirred at 0° C. for one hour.

The reaction solution is poured into 300 ml of water, and the aqueous phase is extracted twice with ethyl acetate, the combined extracts are washed twice with saturated sodium bicarbonate solution and three times with water, dried over magnesium sulfate and concentrated, and impurities are removed from the crude product by column chromatography on 150 g of silica gel (mobile phase methylene chloride/ethyl acetate 8:2, 7:3, 1:1). 3.10 g (87%) of colorless oil are obtained.

$[\alpha]_D^{23} = -32.9°$ (C=1, methanol).

By use of suitable starting materials, the following compounds can be prepared in analogy to the procedure indicated in Example 1:

5-methyl-1,3-dioxolen-2-on-4-ylmethyl 2-[N-(1S-carboxy-3-phenylpropyl)-S-alanyl]-1,2,3,4-tetrahydroisoquinoline-3S-carboxylate;

5-methyl-1,3-dioxolen-2-on-4-ylmethyl 2-[N-[1S-[5-methyl-1,3-dioxolen-2-on-4-ylmethoxycarbonyl]-3-phenylpropyl]-S-alanyl]-1,2,3,4-tetrahydroisoquinoline-3S-carboxylate;

2-[N-[1S-[5-methyl-1,3-dioxolen-2-on-4-ylmethoxycarbonyl]-3-phenylpropyl]-S-alanyl]-1,2,3,4-tetrahydroisoquinoline-3S-carboxylic acid;

5-methyl-1,3-dioxolen-2-on-4-ylmethyl 1-[N-(1S-ethoxycarbonyl-3-phenylpropyl)-S-alanyl]-3'S-spiro[bicyclo-[2.2.2]octane-2,3'-pyrrolidin]-5'S-ylcarboxylate;

5-methyl-1,3-dioxolen-2-on-4-ylmethyl 1-[N-(1S-carboxy-3-phenylpropyl)-S-alanyl]-3'S-spiro[bicyclo[2.2.2]octane-2,3'-pyrrolidin]-5'S-ylcarboxylate;

5-methyl-1,3-dioxolen-2-on-4-ylmethyl 1-[N-[1S-[5-methyl-1,3-dioxolen-2-on-4-ylmethoxycarbonyl]-3-phenylpropyl]-S-alanyl]-3'S-spiro[bicyclo[2.2.2]octane-2,3'-pyrrolidin]-5'S-ylcarboxylate;

1-[N-[1S-[5-methyl-1,3-dioxolen-2-on-4-ylmethoxycarbonyl]-3-phenylpropyl]-S-alanyl]-(2S,3aR,7aS)-octahydro[1H]indole-2-carboxylic acid;

5-methyl-1,3-dioxolen-2-on-4-ylmethyl 2-[N-(1S-ethoxycarbonyl-3-phenylpropyl)-S-alanyl]-1,2,3,4-tetrahydroisoquinoline-3S-carboxylate;

1-[N-[1S[5-methyl-1,3-dioxolen-2-on-4-ylmethoxycarbonyl]-3-phenylpropyl]-S-alanyl]-3'S-spiro-[bicyclo[2.2.2]octane-2,3'-pyrrolidin]-5'S-ylcarboxylic acid;

5-methyl-1,3-dioxolen-2on-4-ylmethyl 1-[N-(1S-ethoxycarbonylbutyl)-S-alanyl]-(2S,3aS,7aS)-octahydro[1H]indole-2-carboxylate 5-methyl-1,3-dioxolen-2-on-4-ylmethyl 1-[N-(1S-carboxybutyl)s-alanyl]-(2S,3aS,7aS)-octahydro[1H]indole-2-carboxylate 5-methyl-1,3-dioxolen-2-on-4-ylmethyl 1-[N-[1S-[5-methyl-1,3-dioxolen-2-on-4-ylmethoxycarbonyl]-butyl]-S-alanyl]-(2S,3aS,7aS)-octahydro[1H]indole-2-carboxylate;

1-[N-[1S-[5-methyl-1,3-dioxolen-2-on-4-ylmethoxycarbonyl]-butyl]-S-alanyl]-(2S,3aS,7aS)-octahydro[1H]indole-2-carboxylic acid;

5-methyl-1,3-dioxolen-2-on-4-ylmethyl 2-[N-(1S-carboxy-3-phenylpropyl)-S-alanyl]-(1S,3S,5S)-2-azabicyclo-[3.3.0]octane-3-carboxylate;

5-methyl-1,3-dioxolen-2-on-4-ylmethyl 2-[N-[1S-[5-methyl-1,3-dioxolen-2-on-4-ylmethoxycarbonyl]-3-phenylpropyl]-S-alanyl]-(1S,3S,5S)-2-azabicyclo[3.3.0]octane-3-carboxylate;

2-[N-[1S-[5-methyl-1,3-dioxolen-2-on-4-ylmethoxycarbonyl]-3-phenylpropyl]-S-alanyl]-(1S,3S,5S)-2-azabicyclo[3.3.0]-octane-3-carboxylic acid;

5-methyl-1,3-dioxolen-2-on-4-ylmethyl 1-[N-(1S-ethoxycarbonyl-3-phenylpropyl)-S-alanyl]-(2S,3aR,7aS)-octahydro[1H]indole-2-carboxylate;

5-methyl-1,3-dioxolen-2-on-4-ylmethyl 1-[N-(1S-carboxy-3-phenylpropyl)-S-alanyl]-(2S,3aR,7aS)-octahydro[1H]indole-2-carboxylate;

5-methyl-1,3-dioxolen-2-on-4-ylmethyl 1-[N-[1S-[5-methyl-1,3-dioxolen-2-on-4-ylmethoxycarbonyl]-3-phenylpropyl]-S-alanyl]-(2S,3aR,7aS)-octahydro[1H]indole-2-carboxylate;

EXAMPLE 2

Benzyl 2-[N-[1S-[5-methyl-1,3-dioxolen-2-on-4-ylmethoxycarbonyl]-3-phenylpropyl]-S-alanyl]-(1S,3S,5S)-2-azabicyclo[3.3.0]octane-3-carboxylate;

2a)

5-Methyl-1,3-dioxolen-2-on-4-ylmethyl 2R-hydroxy-4-phenylbutyrate 9.0 g (0.05 mol) of 2R-hydroxy-4-phenylbutyric acid are dissolved in 200 ml of absolute dimethylformamide, 10.0 g (0.10 mol) of potassium bicarbonate are added, the mixture is stirred at 50° C. for 90 minutes and then, while cooling in ice at 0° C., a solution of 11.6 g (0.06 mol) of 4-bromomethyl-5-methyl-1,3-dioxolen-2-one in 50 ml of absolute dimethylformamide is added dropwise. The mixture is stirred at 0° C. for one hour and then at room temperature for 30 minutes, and is poured into 1 l of water, and the mixture is extracted twice with ethyl acetate. The combined extracts are washed twice with saturated sodium bicarbonate solution and twice with water, dried over sodium sulfate and concentrated, and impurities are removed form the crude product by column chromatography on 600 g of silica gel (mobile phase toluene/ethanol 199:1). 12.6 g (60%) of colorless oil are obtained.

$[\alpha]_D^{25} = -8.2°$ (C=1, methanol).

2b)

5-Methyl-1,3-dioxolen-2-on-4-ylmethyl 4-phenyl-2R-trifluoromethylsulfonyloxybutyrate 5.48 g (18.8 mmol) of the alcohol from a) and 1.6 ml (20 mmol) of absolute pyridien are dissolved in 100 ml of absolute methylene chloride, the solution is cooled to −10° C. and, at this temperature, 5.64 g (20 mmol) of trifluoromethanesulfonic anhydride are added dropwise within 15 minutes. The mixture is then stirred at −10° C. for 10 minutes and then allowed to reach room temperature, and the solvent is evaporated off, the residue is digested in 40 ml of cyclohexane/ethyl acetate 9:1, the insoluble residue is filtered off, and the product solution is purified by column chromatography on 200 g of silica gel (mobile phase cyclohexane/ethyl acetate 9:1, 8:2). 6.5 g (82%) of colorless oil are obtained and are immediately reacted further.

2c)

Benzyl 2-[N-[1S-[5-methyl-1,3-dioxolen-2-on-4-ylmethoxycarbonyl]-3-phenylpropyl]-S-alanyl]-(1S,3S,5S)-2-azabicyclo[3.3.0]octane-3-carboxylate 4.3 g (10.0 mmol) of the trifluoroacetate of benzyl 2-(S-alanyl)-(1S,3S,5S)-2-azabicyclo[3.3.0]octane-3-carboxylate in 25 ml of absolute methylene chloride are mixed with 2.7 ml (20.0 mmol) of absolute triethylamine, the mixture is cooled to 0° C. and, at this temperature, a solution of 6.5 g of the triflate from b) in 50 ml of absolute methylene chloride is added dropwise within 30 minutes. The reaction solution is stirred at room temperature for 30 hours, to stand overnight, diluted with magnesium sulfate and concentrated, and impurities are removed from the crude product (7.7 g) by column chromatography on 400 g of silica gel (mobile phase cyclohexane/ethyl acetate 7:3, 6:4, 1:1, 4:6). 2.0 g (34%) of colorless oil are obtained.

$[\alpha]_D^{25} = -39.5°$ (C=1, methanol).

Using suitable starting materials, it is possible to prepare the following compounds in analogy to the procedure indicated in Example 2:

5-methyl-1,3-dioxolen-2-on-4-ylmethyl 2-[N-[1S-[5-methyl-1,3-dioxolen-2-on-4-ylmethoxycarbonyl]-3-phenylpropyl]-S-alanyl]-(1S,3S,5S)-2-azabicyclo[3.3.0]octane-3-carboxylate;

octyl 2-[N-[1S-[5-methyl-1,3-dioxolen-2-on-4-ylmethoxycarbonyl-]-3-phenylpropyl]-S-alanyl]-(1S,3S,5S)-2-azabicyclo[3.3.0]octane-3-carboxylate;

2-[N-[1S-[5-methyl-1,3-dioxolen-2-on-4-ylmethoxycarbonyl]-3-phenylpropyl]-S-alanyl]-(1S,3S,5S)-2-azabicyclo[3.3.0]octane-3-carboxylic acid;

5-methyl-1,3-dioxolen-2-on-4-methyl 1-[M-[1S-[5-methyl-1,3-dioxolen-2-on-4-ylmethoxycarbonyl]-3-phenylpropyl]-S-alanyl]-(2S,3aR,7aS)-octahydro[1H]indole-2-carboxylate;

benzyl 1-[N-[1S-[5-methyl-1,3-dioxolen-2-on-4-ylmethoxycarbonyl]-3-phenylpropyl]-S-alanyl]-(2S,3aR,7aS)-actahydro[1H]indole-2-carboxylate;

octyl 1-[N-[1S-[5-methyl-1,3-dioxolen-2-on-4-ylmethoxycarbonyl]-3-phenylpropyl]-S-alanyl]-(2S,3aR,7aS)-octahydro[1H]indole-2-carboxylate;

octyl 1-[N-[1S-[5-methyl-1,3-dioxolen-2on-4-ylmethoxycarbonyl]-3-phenylpropyl]-S-alanyl]-(2S,3aR,7aS)-octahydro[1H]indole-2-carboxylate;

1-[N-[1S-[5-methyl-1,3-dioxolen-2-on-4-ylmethoxycarbonyl]-3-phenylpropyl]-S-alanyl]-(2S,3aR,7aS)-octahydro[1H]indole-2-carboxylic acid;

benzhydryl 1-[N-[1S-[5-methyl-1,3-dioxolen-2-on-4-ylmethoxycarbonyl]-3-phenylpropyl]-S-alanyl]-(2S,3aR,7aS)-octahydro[1H]indole-2-carboxylate;

5-methyl-1,3-dioxolen-2-on-4-ylmethyl 2-[N-[1S-[5-methyl-1,3-dioxolen-2-on-4-ylmethoxycarbonyl]-3-phenylpropyl]-S-alanyl]- 1,2,3,4-tetrahydroisoquinoline-3S-carboxylate;

benzyl 2-[N-[1S-[5-methyl-1,3-dioxolen-2-on-4-ylmethoxycarbonyl]-3-phenylpropyl]-S-alanyl]-1,2,3,4-tetrahydroisoquinoline-3S-carboxylate;

2-[N-[1S-[5-methyl-1,3-dioxolen-2-on-4-ylmethoxycarbonyl]-3-phenylpropyl]-S-alanyl]-1,2,3,4-tetrahydroisoquinoline-3S-carboxylic acid;

octyl 2-[N-[1S-[5-methyl-1,3-dioxolen-2on-4-ylmethoxycarbonyl]-3-phenylpropyl]-S-alanyl]-1,2,3,4-tetrahydroisoquinoline-3S-carboxylate;

5-methyl-1,3-dioxolen-2-on-4-ylmethyl 1-[N-[1S-[5-methyl-1,3-dioxolen-2-on-4-ylmethoxycarbonyl]-3-phenylpropyl]-S-alanyl]-3'S-spiro[bicyclo[2.2.2]octane-2,3'-pyrrolidin]-5'S-ylcarboxylate;

benzyl 1-[N-[1S-[5-methyl-1,3-dioxolen-2-on-4-ylmethoxycarbonyl]-3-phenylpropyl]-S-alanyl]-3'S-spiro[bicyclo-[2.2.2]octane-2,3'-pyrrolidin]-5'S-ylcarboxylate;

1-[N-[1S-[5-methyl-1,3-dioxolen-2on-4-ylmethoxycarbonyl]-3-phenylpropyl]-S-alanyl]-3'S-spiro-[bicyclo[2.2.2]octane-2,3'-pyrrolidin]-5'S-ylcarboxylic acid;

octyl 1-[N-[1S-[5-methyl-1,3-dioxolen-2-on-4-ylmethoxycarbonyl]-3-phenylpropyl]-S-alanyl]-3'S-spiro[bicyclo-[2.2.2]octane-2,3'-pyrrolidin]-5'S-ylcarboxylate;

5-methyl-1,3-dioxolen-2-on-4-ylmethyl 1-[N-[1S-[5-methyl-1,3-dioxolen-2-on-4-ylmethoxycarbonyl]-butyl]-S-alanyl]-(2S,3aS,7aS)-octahydro[1H]indole-2-carboxylate;

benzyl 1-[N-[1S-[5-methyl-1,3-dioxolen-2-on-4-ylmethoxycarbonyl]butyl]-S-alanyl]-(2S,3aS,7aS)-octahydro[1H]indole-2-carboxylate;

1-[N-[1S-[5-methyl-1,3-dioxolen-2on-4-ylmethoxycarbonyl]butyl]-S-alanyl]-(2S,3aS,7aS)-octahydro[1H]indole-2-carboxylic acid;

octyl 1-[N-[1S-[5-methyl-1,3-dioxolen-2on-4-ylmethoxycarbonyl]butyl]-S-alanyl]-(2S,3aS,7aS)-octahydro[1H]indole-2-carboxylate.

We claim:

1. A compound of the formula I

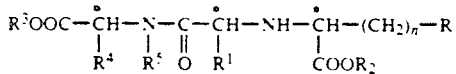 (I)

wherein n is 1 or 2;

R is phenyl or $C_1$-$C_8$ alkyl;

$R^1$ is a side chain of a naturally occurring alpha, amino acid.

$R^2$ and $R^3$ are identical or different and are selected from ($C_1$-$C_6$) alkyl, ($C_6$-$C_{12}$)-aryl-($C_1$-$C_4$)-alkyl and a radical of the formula

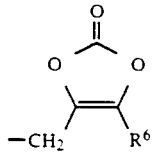

in which $R^6$ is hydrogen or an aliphatic radical having 1-6 carbon atoms.

and where at least one of $R^2$ or $R^3$ denotes said radical;

$R^4$ and $R^5$ together with the atoms carrying them form a ring system selected from octahydroindole, and octahydrocyclopenta[b]pyrrole;

or a physiologically tolerated salt thereof.

2. The compound of claim 1, wherein $R^4$ and $R^5$ are octahydrocyclopenta[b]pyrrole.

3. A pharmaceutical composition comprising an effective amount of the compound as claimed in claim 2 or a physiologically acceptible salt thereof and a physiologically acceptable carrier.

4. A pharmaceutical composition comprising an effective amount of a compound as claimed in claim 1 or a physiologically acceptable salt thereof and a physiologically acceptable carrier.

* * * * *